(12) United States Patent
Himmler

(10) Patent No.: US 7,875,753 B2
(45) Date of Patent: Jan. 25, 2011

(54) 2-BROMO-2,2-DICHLOROETHYL AROMATICS AND PROCESS FOR PREPARATION THEREOF

(75) Inventor: Thomas Himmler, Odenthal (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/725,001

(22) Filed: Mar. 16, 2010

(65) Prior Publication Data
US 2010/0234651 A1    Sep. 16, 2010

(30) Foreign Application Priority Data
Mar. 16, 2009    (EP) .................................. 09155252

(51) Int. Cl.
*C07C 17/00* (2006.01)
*C07C 22/00* (2006.01)

(52) U.S. Cl. ...................................... 570/191; 570/185

(58) Field of Classification Search ................. 570/185, 570/191
See application file for complete search history.

(56) References Cited

U.S. PATENT DOCUMENTS

| 4,145,362 A | 3/1979 | Brepoels et al. |
| 5,994,274 A | 11/1999 | Fischer et al. |
| 2006/0160847 A1 | 7/2006 | Fischer et al. |

FOREIGN PATENT DOCUMENTS

| DE | 20 16 809 A1 | 10/1970 |
| EP | 0 123 187 A2 | 10/1984 |

OTHER PUBLICATIONS

Minghong et al., simultaneous determination of trace levels of nine haloacetic acid in biological samples, (Analytical chemistry (2003), 75 (16), 4065-4080).*

Ando, A., et al., "Synthesis of (2,2,2-Trifluoroethyl)benzene Derivatives," *J. Org. Chem.*, 53:3637-3639, American Chemical Society, United States (1988).

Dombrovskii, A.V. & Naidan, V.M., "Haloarylation of Unsaturated Comopunds with Aromatic Diazo Compounds," *Russian Journal of General Chemistry* (*Zhurnal Obshchei Khimil*), 32:1282-1284, Pleiades Publishing, Russia (1962).

Freidlina, R.Kh., et al., *Doklady-Akademii Nauk SSSR*, 236:637-640, Russia (1977).

Meerwein, Von Hans, et al., "Über die Einwirkung aromatischer Diazoverbindungen auf α,β-ungesättigte Carbonylverbindungen," *Journal füe praktische Chemie*, 152:237-266, Germany (1939).

Naidan, V.M. & Dombrovskii, A.V., "A New Method for the Production of Arylacetic Acids," Translated from *Zhurnal Obshchei Khimil*,34(5):1469-1473, Pleiades Publishing, Russia (1964).

Naidan, V.M., *Nauk. Zap.*, 51:40-42, Chernivets'k. Derzh. Univ., Ser. Prirodn, Russia (1961).

Reeve, W. & Tsuk, R., "Reactions of (Trihalomethyl)carbinols with Aqueous Potassium Hydroxide," *J. Org. Chem.*, 45:5214-5215, American Chemical Society, United States (1980).

English language Abstract of European Patent Publication No. EP 0 123 187 A2 (1984).

European Search Report for European Application No. EP 09 15 5252, European Patent Office, Netherlands, mailed on Aug. 27, 2009.

International Search Report for International Application No. PCT/EP2010/001300, European Patent Office, Netherlands, mailed on Feb. 7, 2010.

* cited by examiner

*Primary Examiner*—Jafar Parsa
(74) *Attorney, Agent, or Firm*—Sterne, Kessler, Goldstein & Fox P.L.L.C.

(57) ABSTRACT

The present invention relates to novel 2-bromo-2,2-dichloroethyl aromatics of the formula (V)

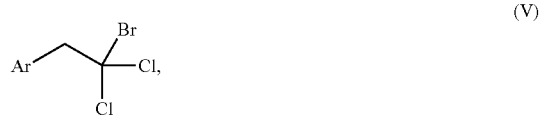

in which Ar is as defined above and to processes for preparation thereof.

11 Claims, No Drawings

2-BROMO-2,2-DICHLOROETHYL AROMATICS AND PROCESS FOR PREPARATION THEREOF

The present invention relates to novel 2-bromo-2,2-dichloroethyl aromatics and to processes for preparation thereof.

It is already known that olefins can be arylated using aryldiazonium halides in the presence of a catalyst (Meerwein reaction: H. Meerwein et al., *Journal für praktische Chemie* 152 (1939), 237-266).

The use of vinylidene chloride (1,1-dichloroethylene) as the olefin leads to the formation of 2,2,2-trichloroethyl aromatics of the formula (I) (see, for example: A. V. Dombrovskii and V. M. Naidan, *Zhurnal Obshchei Khimii* 32 (1962) 1282-4; A. Ando et al., *J. Org. Chem.* 53 (1988) 3637-9); V. M. Naidan, *Nauk. Zap., Chemivets 'k. Derzh. Univ., Ser. Prirodn. Nauk* 51 (1961) 40-2 (CAN 62:58612)).

The 2,2,2-trichloroethyl aromatics of the formula (I) thus prepared serve, for example, as intermediates for synthesis of phenylacetic acids (V. M. Naidan and A. V. Dombrovskii, *Zhurnal Obshchei Khimii*, 34 (1964) 1469-73; EP-A-835243; EP-A-123187).

Phenylacetic acids are important intermediates, for example for preparing pharmaceutical compounds or agrochemicals (see, for example, EP-A-835243; WO2004/065366).

The synthesis of 2,2,2-trichloroethyl aromatics of the formula (I) by arylating vinylidene chloride is generally effected in two steps:

First, in the first step, the corresponding aniline is diazotized, and then, in a second step, the aryldiazonium salt thus obtained is reacted with vinylidene chloride in the presence of a copper catalyst.

The diazotization of the aniline can be performed either under nonaqueous conditions or in aqueous systems, in a manner which is known in principle.

In the case of diazotization in the absence of water, the aniline is diazotized in an inert organic solvent, for example acetonitrile in the presence of chloride ions with an organic nitrite, for example n-butyl nitrite, isoamyl nitrite or tert-butyl nitrite.

However, it has also already become known to perform the Meerwein arylation in such a way that the diazotization is performed in the presence of water by means of sodium nitrite and hydrochloric acid, and then the diazonium chloride is reacted with vinylidene chloride (J. R. Brepoels et al., DE-A-2016809).

However, a disadvantage of these known processes is that frequently only moderate or even only poor yields of 2,2,2-trichloroethyl aromatics ("Meerwein product") are obtained. The reason for this is essentially the formation of by-products, which include especially the product of a Sandmeyer reaction of the formula (II) ("Sandmeyer product") and 2,2,4,4,4-pentachlorobutyl aromatics of the formula (III).

These conditions can be illustrated by the following reaction scheme:

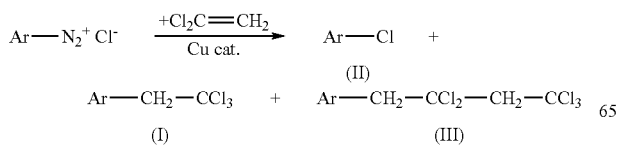

The degree in which these and other by-products are formed depends upon factors including the reactivity of the corresponding diazonium salt.

The formation of 2,2,4,4,4-pentachlorobutyl aromatics of the formula (III) has also already been described (R. Kh. Freidlina et al., *Doklady Akademii Nauk SSSR* 236 (1977) 637-40).

The present situation is also that the target product of the formula (I) forms by reaction of the diazonium salt with one molecule of vinylidene chloride, the by-product of the formula (II) by reaction of the diazonium salt without vinylidene chloride, and the by-product of the formula (III) with 2 molecules of vinylidene chloride. Accordingly, in the case of a high proportion of Sandmeyer product of the formula (II), the latter can be suppressed by using a greater excess of vinylidene chloride; however, as expected, this in many cases increases the proportion of by-product of the formula (III). This can lead to the effect that the yield remains substantially unchanged over a relatively wide range of the molar ratio of vinylidene chloride to aryldiazonium salt, and, instead, only the ratio of the by-products (II) and (III) changes. As a result, an increase in the yield of compound of the formula (I) is often barely possible.

There is thus still a lack of an effective, general method, which provides good yields, for preparing phenylacetic acids proceeding from anilines via the arylation of vinylidene chloride.

It has now been found that vinylidene chloride can be arylated with aryldiazonium bromides of the formula (IV) to give 2-bromo-2,2-dichloroethyl aromatics of the formula (V), forming the corresponding 4-bromo-2,2,4,4-tetrachlorobutyl aromatics of the formula (VI) surprisingly either not at all or only in an insignificant amount. It thus now becomes possible, by virtue of greater excesses of vinylidene chloride, to suppress the proportion of Sandmeyer product of the formula (VII) and thus to significantly increase the yields of 2-bromo-2,2-dichloroethyl aromatics of the formula (V).

The reaction is illustrated by the following scheme:

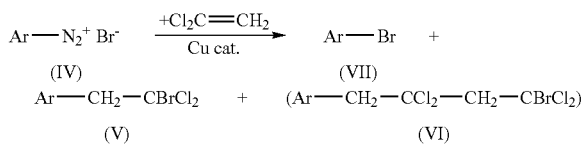

The inventive 2-bromo-2,2-dichloroethyl aromatics of the formula (V)

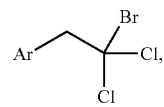

in which
Ar is a radical of the formula (VIII)

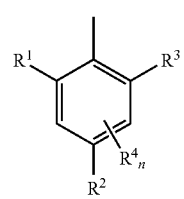

in which

R$^1$, R$^2$ and R$^3$ are the same or different and are each independently hydrogen, C$_1$-C$_6$-alkyl, optionally substituted C$_6$-C$_{10}$-aryl, nitro, cyano, halogen, C$_1$-C$_4$-alkoxy, C$_1$-C$_4$-alkylthio or C$_6$-C$_{10}$-aryloxy, R$^4$ is C$_1$-C$_6$-alkyl, optionally substituted C$_6$-C$_{10}$-aryl, nitro, cyano, halogen, C$_1$-C$_4$-alkoxy, C$_1$-C$_4$-alkylthio or C$_6$-C$_{10}$-aryloxy and n is 0 or 1 are novel.

Preferably,

R$^1$, R$^2$ and R$^3$ are the same or different and are each independently hydrogen, methyl, ethyl, n-propyl, isopropyl, n-butyl, tert-butyl, isobutyl, sec-butyl, optionally substituted C$_6$-aryl, fluorine, chlorine, bromine, methoxy, ethoxy, n-propoxy, isopropoxy, n-butoxy, isobutoxy, sec-butoxy or tert-butoxy, R$^4$ is methyl, ethyl, n-propyl, isopropyl, n-butyl, tert-butyl, isobutyl, sec-butyl, optionally substituted C$_6$-aryl, fluorine, chlorine, bromine, methoxy, ethoxy, n-propoxy, isopropoxy, n-butoxy, isobutoxy, sec-butoxy or tert-butoxy, n is 0 or 1.

More preferably,

R$^1$, R$^2$ and R$^3$ are the same or different and are each independently hydrogen, methyl, ethyl, phenyl, chlorine or bromine, R$^4$ is methyl, ethyl, phenyl, chlorine or bromine, n is 0 or 1.

Most preferably,

R$^1$ is methyl, ethyl or chlorine,

R$^2$ is chlorine,

R$^3$ is hydrogen, methyl or bromine,

R$^4$ is methyl, n is 0 or 1.

In the definitions of the symbols given in the above formulae, collective terms were used, which are generally representative of the following substituents:

Halogen: fluorine, chlorine, bromine and iodine;

Alkyl: saturated, straight-chain or branched hydrocarbon radicals having 1 to 6 carbon atoms, for example C$_1$-C$_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Aryl: mono-, bi- or polycyclic aromatic system having preferably 6 to 10 carbon atoms, for example phenyl, naphthyl, preferably phenyl; polycyclic systems such as tetrahydronaphthyl, indenyl, indanyl, where the bonding site is on the aromatic system; the aryl groups may be substituted by one or more identical or different radicals. Examples of substituted aryls are the arylalkyls, which may likewise be substituted by one or more identical or different radicals in the alkyl and/or aryl moiety, such as benzyl and 1-phenylethyl.

The aryldiazonium bromides of the formula (IV) in which the Ar radical is as defined in formula (VIII) can be prepared in a manner known in principle.

To this end, for example, the aniline ArNH$_2$ of the formula (IX) in which the Ar radical may be as defined above is diazotized by reaction with an alkyl nitrite in an inert organic solvent in the presence of inorganic bromides.

Useful inert organic solvents include, for example, acetonitrile, propionitrile, toluene, chlorobenzene, dichlorobenzene, methylene chloride, 1,2-dichloroethane, methanol or ethanol.

The alkyl nitrites used may, for example, be methyl nitrite, ethyl nitrite, propyl nitrite, n-butyl nitrite, tert-butyl nitrite or isoamyl nitrite.

Useful inorganic bromides include, for example, alkali metal or alkaline earth metal bromides, for example NaBr, KBr, LiBr, MgBr$_2$. In addition, it is also possible to use Cu(I) Br or Cu(II) Br$_2$ directly. These inorganic bromides are typically used in amounts of 0.8 to 2 mol per mole of aniline of the formula (IX); preference is given to amounts of 1 to 1.5 mol per mole.

In another embodiment, the aniline of the formula (IX) is diazotized by known methods, by reaction with an inorganic nitrite and hydrogen bromide in the presence of water.

The reaction can be effected in water alone or in a mixture of water and a water-miscible organic solvent. Examples of water-miscible organic solvents include acetic acid, propionic acid, acetone, methyl ethyl ketone, methanol, ethanol and acetonitrile.

The inorganic nitrites used are alkali metal nitrites. Preference is given to sodium nitrite and potassium nitrite.

The inorganic nitrites are used typically in a slight excess based on the aniline.

The temperature in the diazotization is guided mainly by the thermal stability of the diazonium bromide obtained. It is usual to work between −50 and +50° C. Preference is given to temperatures between −30 and +30° C.

In the process according to the invention, the aryldiazonium bromides of the formula (IV) are then reacted in the presence of a copper catalyst with vinylidene chloride and a bromide source.

The amount of vinylidene chloride may vary within wide limits. It is usual to work with an amount between 1 and 100 mol of vinylidene chloride per mole of aryldiazonium bromide. Preferred amounts are between 3 and 70 mol per mole, particularly preferred amounts between 5 and 50 mol of vinylidene chloride per mole of aryldiazonium bromide.

The copper catalysts used may be copper(I) or copper(II) halides such as CuCl, CuBr, CuCl$_2$, CuBr$_2$, CuI, and copper (I) or copper(II) oxide. Since copper chlorides form not only the inventive compounds of the formula (V) but also the trichloro compounds of the formula (I), preference is given to using CuBr, CuBr$_2$, Cu$_2$O or CuO. Particular preference is given to CuBr or CuBr$_2$.

The amount of copper catalyst can be varied within wide limits. It is usual to take no more catalyst than is needed for a very substantially complete conversion of the aryldiazonium bromide within an acceptable time. The amount may accordingly be between 1 and 100 mol percent. Preference is given to 5 to 75 mol percent.

The bromide sources used are alkali metal or alkaline earth metal bromides, examples including lithium bromide, sodium bromide, potassium bromide or magnesium bromide. Preference is given to lithium bromide.

The amount of alkali metal or alkaline earth metal bromide can be varied within wide limits. Preference is given to using 25 to 500 mol of bromide per mole of diazonium bromide of the formula (IV). Particular preference is given to 50 to 300 mol per mole.

The reaction temperature of the process according to the invention can be varied within wide limits. Preference is given to working at temperatures of −30 to +60° C., more preferably between −20 and +40° C.

The reaction time of the process according to the invention is not critical. The reaction time selected will typically be that needed for a very substantial conversion of the reactants. This time is typically between 1 and 12 hours.

EXAMPLES

Example 1

1-Bromo-2-(2'-bromo-2',2'-dichloroethyl)-5-chloro-3-ethylbenzene

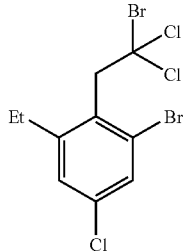

At room temperature, 9.38 g [0.04 mol] of 2-bromo-4-chloro-6-ethylaniline are introduced into 30 ml of 36% aqueous HBr, the mixture is cooled to −10 to −5° C., and a solution, cooled to 0° C., of 3.31 g [0.048 mol] of NaNO₂ in 15 ml of water is added dropwise within 15 minutes. Subsequently, the mixture is stirred at −10 to −5° C. for 15 minutes. It is then admixed with a solution, cooled to 0° C., of 0.24 g of urea in 75 ml of water, and then 5.36 g [0.024 mol] of copper(II) bromide and 1.74 g [0.02 mol] of LiBr are added. To this mixture is added dropwise, at −10 to −5° C. within 30 minutes, a solution of 67.83 g [0.7 mol=17.5 molar equivalents] of vinylidene chloride in 130 ml of acetone. The mixture is allowed to come to room temperature with good stirring and left to react for another 3 hours. The reaction mixture is diluted with 100 ml of water and extracted twice with 70 ml each time of MTBE. The combined organic phases are washed with 30 ml of water, dried over sodium sulphate and concentrated under reduced pressure. This gives 15.7 g of oil which, according to GC-MS, contains 84.3 area percent (area %) of 1-bromo-2-(2'-bromo-2',2'-dichloroethyl)-5-chloro-3-ethylbenzene. This corresponds to a yield of 83.7% of theory.

Comparative Example 1-1

1-Bromo-2-(2',2',2'-trichloroethyl)-5-chloro-3-ethylbenzene

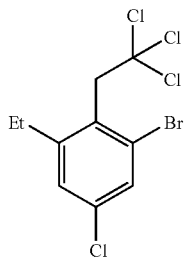

To a solution of 4.83 g [0.045 mol] of tert-butyl nitrite in 15 ml of acetonitrile are added 2.42 g [0.018 mol=0.6 molar equivalent] of copper(II) chloride and then, dropwise, 14.54 g [0.15 mol=5 molar equivalents] of vinylidene chloride within 30 minutes. The mixture is stirred at room temperature for 15 to 20 minutes and then a solution of 7.04 g [0.03 mol] of 2-bromo-4-chloro-6-ethylaniline in 5 ml of acetonitrile is added dropwise at room temperature within 15 minutes. The mixture is stirred at room temperature for 3 hours and then worked up as described in Example 1. This results in 11.13 g of oil which, according to GC-MS, contains 66.1 area % of 1-bromo-2-(2',2',2'-trichloroethyl)-5-chloro-3-ethylbenzene. This corresponds to a yield of 66.1% of theory.

The GC-MS indicates, as by-products, 5.5 area % of Sandmeyer product and 4.2 area % of 1-bromo-5-chloro-3-ethyl-2-(2',2',4',4',4'-pentachlorobutyl)benzene.

Comparative Example 1-2

1-Bromo-2-(2',2',2'-trichloroethyl)-5-chloro-3-ethylbenzene

The procedure is as in Comparative Example 1-1, except that 21.8 g [0.225 mol=7.5 molar equivalents] of vinylidene chloride are used. This gives 9.54 g of oil which, according to GC-MS, contains 72.9 area % of 1-bromo-2-(2',2',2'-trichloroethyl)-5-chloro-3-ethylbenzene. This corresponds to a yield of 66.1% of theory.

The GC-MS indicates, as by-products, 8.3 area % of Sandmeyer product and 3.7 area % of 1-bromo-5-chloro-3-ethyl-2-(2',2',4',4',4'-pentachlorobutyl)benzene.

Comparative Example 1-3

1-Bromo-2-(2',2',2'-trichloroethyl)-5-chloro-3-ethylbenzene

The procedure is as in Comparative Example 1-1, except that 29.08 g [0.3 mol=10 molar equivalents] of vinylidene chloride are used. This gives 9.48 g of oil which, according to GC-MS, contains 71.5 area % of 1-bromo-2-(2',2',2'-trichloroethyl)-5-chloro-3-ethylbenzene. This corresponds to a yield of 64.4% of theory.

The GC-MS indicates, as by-products, 7.4 area % of Sandmeyer product and 4.5 area % of 1-bromo-5-chloro-3-ethyl-2-(2',2',4',4',4'-pentachlorobutyl)benzene.

Comparative Example 1-4

1-Bromo-2-(2',2',2'-trichloroethyl)-5-chloro-3-ethylbenzene

The procedure is as in Comparative Example 1-1, except that 43.62 g [0.45 mol=15 molar equivalents] of vinylidene chloride are used. This gives 10.46 g of oil which, according to GC-MS, contains 70.8 area % of 1-bromo-2-(2',2',2'-trichloroethyl)-5-chloro-3-ethylbenzene. This corresponds to a yield of 70.4% of theory.

The GC-MS indicates, as by-products, 2.8 area % of Sandmeyer product and 8.9 area % of 1-bromo-5-chloro-3-ethyl-2-(2',2',4',4',4'-pentachlorobutyl)benzene.

Comparative Example 1-5

1-Bromo-2-(2',2',2'-trichloroethyl)-5-chloro-3-ethylbenzene

The procedure is as in Comparative Example 1-4, except that 4.84 g [0.036 mol=1.2 molar equivalents] of copper(II) chloride are used. This gives 10.36 g of oil which, according to GC-MS, contains 74.5 area % of 1-bromo-2-(2',2',2'-trichloroethyl)-5-chloro-3-ethylbenzene. This corresponds to a yield of 73.4% of theory.

The GC-MS indicates, as by-products, 1.9 area % of Sandmeyer product and 10.7 area % of 1-bromo-5-chloro-3-ethyl-2-(2',2',4',4',4'-pentachlorobutyl)benzene.

Example 2

1-(2'-Bromo-2',2'-dichloroethyl)-2,4-dichloro-5-methylbenzene

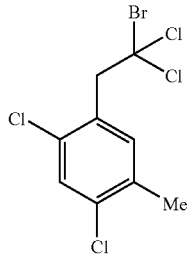

At room temperature, 7.04 g [0.04 mol] of 2,4-dichloro-5-methylaniline are introduced into 30 ml of 36% aqueous HBr, the mixture is cooled to −10 to −5° C. and a solution, cooled to 0° C., of 3.31 g [0.048 mol] of NaNO$_2$ in 80 ml of water is added dropwise within 60 minutes. Subsequently, the mixture is stirred at −10 to −5° C. for 15 minutes. Subsequently, 1.79 g [0.008 mol] of copper(II) bromide and 6.95 g [0.08 mol] of LiBr are added. To this mixture is added dropwise, at −10 to −5° C. within 30 minutes, a solution of 38.8 g [0.4 mol=10 molar equivalents] of vinylidene chloride in 130 ml of acetone. The mixture is allowed to come to room temperature with good stirring and left to react for another 3 hours. The reaction mixture is diluted with 100 ml of water and extracted twice with 70 ml each time of MTBE. The combined organic phases are washed with 30 ml of water, dried over sodium sulphate and concentrated under reduced pressure. This gives 12.8 g of oil which, according to GC-MS, contains 92 area % of 1-(2'-bromo-2',2'-dichloroethyl)-2,4-dichloro-5-methylbenzene. This corresponds to a yield of 87.4% of theory.

The GC-MS shows, as by-products, 3.3 area % of Sandmeyer product and 1.2 area % of 1-(4-bromo-2',2',4',4'-tetrachlorobutyl)-2,4-dichloro-5-methylbenzene.

Comparative Example 2-1

1-(2',2',2'-Trichloroethyl)-2,4-dichloro-5-methylbenzene

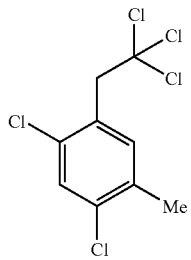

At room temperature, 7.04 g [0.04 mol] of 2,4-dichloro-5-methylaniline are introduced into 28 ml of conc. hydrochloric acid, the mixture is cooled to −5 to 0° C. and a solution, cooled to 0° C., of 3.31 g [0.048 mol] of NaNO$_2$ in 80 ml of water is added dropwise within 60 minutes. Subsequently, the mixture is stirred at −5 to 0° C. for 15 minutes. Subsequently, 3.23 g [0.024 mol] of copper(II) chloride are added. To this mixture is added dropwise, at 0° C. within 30 minutes, a solution of 38.8 g [0.4 mol=10 molar equivalents] of vinylidene chloride in 130 ml of acetone. The mixture is allowed to come to room temperature with good stirring and left to react for another 3 hours. The reaction mixture is diluted with 100 ml of water and extracted twice with 70 ml each time of MTBE. The combined organic phases are washed with 30 ml of water, dried over sodium sulphate and concentrated under reduced pressure. This gives 12.3 g of oil which, according to GC-MS, contains 64.05 area % of 1-(2',2',2'-trichloroethyl)-2,4-dichloro-5-methylbenzene. This corresponds to a yield of 67.4% of theory.

The GC-MS shows, as by-products, 5.7 area % of Sandmeyer product and 23.8 area % of 1,5-dichloro-2-methyl-4-(2',2',4',4',4'-pentachlorobutyl)benzene.

Example 3

2-(2-Bromo-2,2-dichloroethyl)-5-chloro-1,3-dimethylbenzene

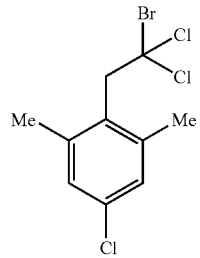

At room temperature, 6.22 g [0.04 mol] of 4-chloro-2,6-dimethylaniline are introduced into 30 ml of 36% aqueous HBr, the mixture is cooled to −10 to −5° C. and a solution, cooled to 0° C., of 3.31 g [0.048 mol] of NaNO$_2$ in 80 ml of water is added dropwise within 60 minutes. Subsequently, the mixture is stirred at −10 to −5° C. for 15 minutes. Then 1.79 g [0.008 mol] of copper(II) bromide and 6.95 g [0.08 mol] of LiBr are added. To this mixture is added dropwise, at −10 to −5° C. within 30 minutes, a solution of 58.1 g [0.6 mol=15 molar equivalents] of vinylidene chloride in 130 ml of acetone. The mixture is allowed to come to room temperature with good stirring and left to react for another 3 hours. The reaction mixture is diluted with 100 ml of water and extracted twice with 70 ml each time of MTBE. The combined organic phases are washed with 30 ml of water, dried over sodium sulphate and concentrated under reduced pressure. This gives 10.3 g of oil which, according to GC-MS, contains 62 area % of 2-(2-bromo-2,2-dichloroethyl)-5-chloro-1,3-dimethylbenzene. This corresponds to a yield of 50.5% of theory.

The GC-MS shows, as a by-product, 0.7 area % of 2-(4-bromo-2,2,4,4-tetrachlorobutyl)-5-chloro-1,3-dimethylbenzene.

Comparative Example 3-1

2-(2,2,2-Trichloroethyl)-5-chloro-1,3-dimethylbenzene

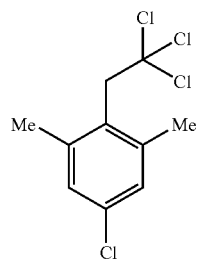

At room temperature, 6.22 g [0.04 mol] of 4-chloro-2,6-dimethylaniline are introduced into 28 ml of 32% aqueous HCl, the mixture is cooled to −10 to −5° C. and a solution, cooled to 0° C., of 3.31 g [0.048 mol] of NaNO$_2$ in 80 ml of water is added dropwise within 60 minutes. Subsequently, the mixture is stirred at −10 to −5° C. for 15 minutes. Then 3.23 g [0.024 mol] of copper(II) chloride are added. To this mixture is added dropwise, at −10 to −5° C. within 30 minutes, a solution of 58.1 g [0.6 mol=15 molar equivalents] of vinylidene chloride in 130 ml of acetone. The mixture is allowed to come to room temperature with good stirring and left to react for another 3 hours. The reaction mixture is diluted with 100 ml of water and extracted twice with 70 ml each time of MTBE. The combined organic phases are washed with 30 ml of water, dried over sodium sulphate and concentrated under reduced pressure. This gives 5.4 g of oil which, according to GC-MS, contains 38.4 area % of 2-(2,2,2-trichloroethyl)-5-chloro-1,3-dimethylbenzene. This corresponds to a yield of 19.1% of theory.

The GC-MS indicates, as a by-product, 11.0 area % of 2-(2,2,4,4, 4-pentachlorobutyl)-5-chloro-1,3-dimethylbenzene.

Example 4

Methyl 2-bromo-4-chloro-6-ethylphenylacetate

To a solution of 15.8 g [0.04 mol] of 1-bromo-2-(2'-bromo-2',2'-dichloroethyl)-5-chloro-3-ethylbenzene in 35 ml of methanol is added dropwise, at 10-20° C., 43 g of a 30% solution of NaOMe in MeOH [0.24 mol]. The mixture is subsequently heated to reflux for 5 hours, then cooled to room temperature, 12.3 g of conc. sulphuric acid are added and the mixture is heated again to reflux for 2 hours. The reaction mixture is cooled to room temperature and then metered in portions into a suspension of 12.7 g of NaHCO$_3$ in 80 ml of water, stirred with 50 ml of methylene chloride and filtered through silica gel, and the filtercake is washed three times with 20 ml each time of methylene chloride. The combined organic phases are extracted by shaking with 20 ml of water and then 20 ml of saturated aqueous NaCl solution, dried over sodium sulphate and concentrated under reduced pressure. This gives 11.55 g of methyl 2-bromo-4-chloro-6-ethylphenylacetate (99% of theory).

The invention claimed is:

1. Compounds of the formula (V)

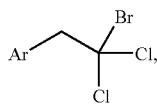

(V)

in which
Ar is a radical of the formula (VIII)

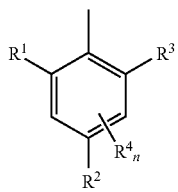

(VIII)

in which
R$^1$, R$^2$ and R$^3$ are the same or different and are each independently hydrogen, C$_1$-C$_6$-alkyl, optionally substituted C$_6$-C$_{10}$-aryl, nitro, cyano, halogen, C$_1$-C$_4$-alkoxy, C$_1$-C$_4$-alkylthio or C$_6$-C$_{10}$-aryloxy,
R$^4$ is C$_1$-C$_6$-alkyl, optionally substituted C$_6$-C$_{10}$-aryl, nitro, cyano, halogen, C$_1$-C$_4$-alkoxy, C$_1$-C$_4$-alkylthio or C$_6$-C$_{10}$-aryloxy and
n is 0 or 1.

2. Compounds of the formula (V) according to claim 1, in which
R$^1$, R$^2$ and R$^3$ are the same or different and are each independently hydrogen, methyl, ethyl, n-propyl, isopropyl, n-butyl, tert-butyl, isobutyl, sec-butyl, optionally substituted C$_6$-aryl, fluorine, chlorine, bromine, methoxy, ethoxy, n-propoxy, isopropoxy, n-butoxy, isobutoxy, sec-butoxy or tert-butoxy,
R$^4$ is methyl, ethyl, n-propyl, isopropyl, n-butyl, tert-butyl, isobutyl, sec-butyl, optionally substituted C$_6$-aryl, fluorine, chlorine, bromine, methoxy, ethoxy, n-propoxy, isopropoxy, n-butoxy, isobutoxy, sec-butoxy or tert-butoxy,
n is 0 or 1.

3. Compounds of the formula (V) according to claim 1, in which
R$^1$, R$^2$ and R$^3$ are the same or different and are each independently hydrogen, methyl, ethyl, phenyl, chlorine or bromine,
R$^4$ is methyl, ethyl, phenyl, chlorine or bromine,
n is 0 or 1.

4. Compounds of the formula (V) according to claim 1, in which
R$^1$ is methyl, ethyl or chlorine,
R$^2$ is chlorine,
R$^3$ is hydrogen, methyl or bromine,
R$^4$ is methyl,
n is 0 or 1.

5. Process for preparing compounds of the formula (V) according to claim 1, characterized in that compounds of the formula (IV)

Ar—N$_2$$^+$Br$^-$ (IV)

in which Ar is as defined above
are reacted with vinylidene chloride in the presence of a copper salt and a bromide source.

6. Process according to claim 5, characterized in that the copper salts used are copper(I) or copper(II) halides or copper (I) or copper(II) oxide.

7. Process according to claim 5, characterized in that the copper salts used are CuCl, CuBr, CuCl$_2$, CuBr$_2$ or CuI.

8. Process according to claim 5, characterized in that the copper salts used are CuBr or CuBr$_2$.

9. Process according to claim 5, characterized in that the copper salts used are Cu$_2$O or CuO.

10. Process according to claim 5, characterized in that the vinylidene chloride is used in amounts between 1 and 100 mol of vinylidene chloride per mole of aryldiazonium bromide.

11. Process according to claim 5, characterized in that the vinylidene chloride is used in amounts between 5 and 50 mol of vinylidene chloride per mole of aryldiazonium bromide.

* * * * *